(12) United States Patent
Lei

(10) Patent No.: US 7,688,450 B2
(45) Date of Patent: Mar. 30, 2010

(54) HYDROGEL-ACTUATED MICROMIRRORS FOR OPTICAL SENSING

(75) Inventor: Ming Lei, Chandler, AZ (US)

(73) Assignee: Intel Corporation, Santa Clara, CA (US)

( * ) Notice: Subject to any disclaimer, the term of this patent is extended or adjusted under 35 U.S.C. 154(b) by 374 days.

(21) Appl. No.: 11/753,736

(22) Filed: May 25, 2007

(65) Prior Publication Data

US 2008/0291424 A1    Nov. 27, 2008

(51) Int. Cl.
*G01N 21/55* (2006.01)
(52) U.S. Cl. ................ 356/445; 356/244; 356/39
(58) Field of Classification Search ......... 356/244–246, 356/445, 39
See application file for complete search history.

(56) References Cited

U.S. PATENT DOCUMENTS 6,421,128 B1 * 7/2002 Salamon et al. .............. 356/445
7,317,533 B2 * 1/2008 Chiarello et al. ............. 356/445

OTHER PUBLICATIONS

Ming Lei et al., "High-Resolution Technique for Fabricating Environmentally Sensitive Hydrogel Microstructures", Langmuir, The ACS Journal of Surfaces and Colloids, 2004, vol. 20, No. 21, pp. 8947-8951.
David J. Beebe et al., "Functional Hydrogel Structures for Autonomous Flow Control Inside Microfluidic Channels", Nature, vol. 404, Apr. 6, 2000, www.nature.com, pp. 588-590.

* cited by examiner

*Primary Examiner*—L. G Lauchman
(74) *Attorney, Agent, or Firm*—Kevin A. Reif

(57) ABSTRACT

A thin, deformable member may be fixed at one end, while another portion of the member rests on a hydrogel substance whose thickness changes depending on a characteristic of a liquid that permeates the hydrogel. When the hydrogel changes thickness and causes part of the member to tilt, a reflective surface on the member may reflect light in a different direction. Appropriate sensors may detect the change in the direction of the reflected light, allowing determination of the change in thickness, which in turn permits determination of the relevant characteristic of the liquid.

11 Claims, 4 Drawing Sheets

HYDROGEL-ACTUATED MICROMIRRORS FOR OPTICAL SENSING

BACKGROUND

In various areas of medical, chemical, and/or biological technology, it is often desirable to measure the properties of an aqueous solution. For example, it might be desirable to measure pH, temperature, glucose concentration, etc, which typically requires a customized procedure for each type of measurement. Older techniques frequently involve mixing another chemical in the solution and looking for a detectable change, such as a change in color, a change in electrical conductivity, the production of salts, etc.

More recent techniques may use a hydrogel substance that changes its thickness based on the pertinent characteristics of the solution as that solution permeates the hydrogel. If the hydrogel substance is a few millimeters in size, it may take a long time (e.g., hours) for the solution to permeate the hydrogel substance to produce the desired change in thickness. Reducing the size to a few micrometers may reduce the time to permeate and the resulting time to get an accurate reading to a few seconds. However, directly measuring a change in thickness of only a few micrometers may be difficult and expensive.

BRIEF DESCRIPTION OF THE DRAWINGS

Some embodiments of the invention may be understood by referring to the following description and accompanying drawings that are used to illustrate embodiments of the invention. It should be understood that the illustrations of physical structures are not drawn to scale, and no inference should be drawn from the relative dimensions of those structures as depicted in the drawings. In the drawings.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure an understanding of this description.

References to "one embodiment", "an embodiment", "example embodiment", "various embodiments", etc., indicate that the embodiment(s) of the invention so described may include particular features, structures, or characteristics, but not every embodiment necessarily includes the particular features, structures, or characteristics. Further, some embodiments may have some, all, or none of the features described for other embodiments.

In the following description and claims, the terms "coupled" and "connected," along with their derivatives, may be used. It should be understood that these terms are not intended as synonyms for each other. Rather, in particular embodiments, "connected" is used to indicate that two or more elements are in direct physical or electrical contact with each other. "Coupled" is used to indicate that two or more elements co-operate or interact with each other, but they may or may not be in direct physical or electrical contact.

As used in the claims, unless otherwise specified the use of the ordinal adjectives "first", "second", "third", etc., to describe a common element, merely indicate that different instances of like elements are being referred to, and are not intended to imply that the elements so described must be in a given sequence, either temporally, spatially, in ranking, or in any other manner.

Some embodiments of the invention may use changes in the thickness of a hydrogel to raise or lower a portion of a thin, deformable, and substantially planar member. One end of the member may be fixed, while another portion of the member may rest on the hydrogel, so that the change in thickness of the hydrogel causes a change in the angle of the plane of the member. By having a reflective surface on the member, the reflective surface will also change its angle in response to changes in the hydrogel thickness. When a laser or other precisely-controllable form of light is reflected from the member, the change of angle will change the direction of the reflected light, and this change in direction can be detected with an inexpensive sensor. Because the various embodiments described herein may be fabricated in very small dimension, the reflective surface may sometimes be referred to as a 'micromirror', but various embodiments are not limited to devices that use this term.

Figure 1A:
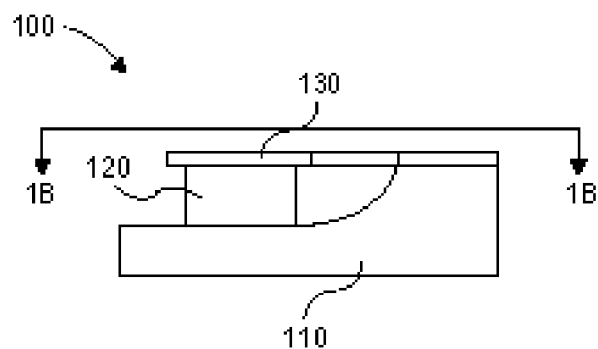
FIGS. 1A, 1B, and 1C show views of a hydrogel-actuated sensor module, according to an embodiment of the invention.
Figure 1B:
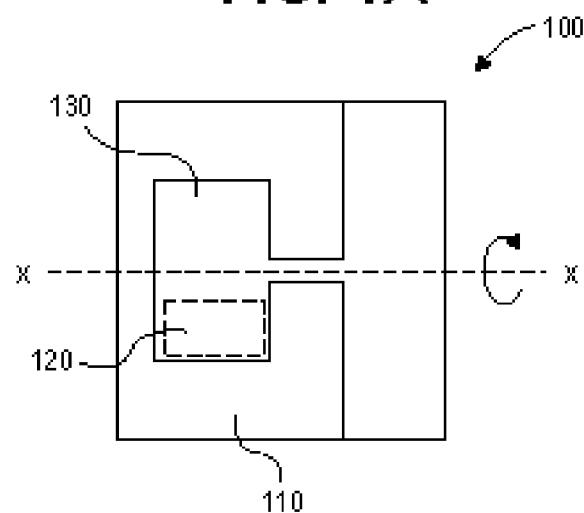
Figure 1C:
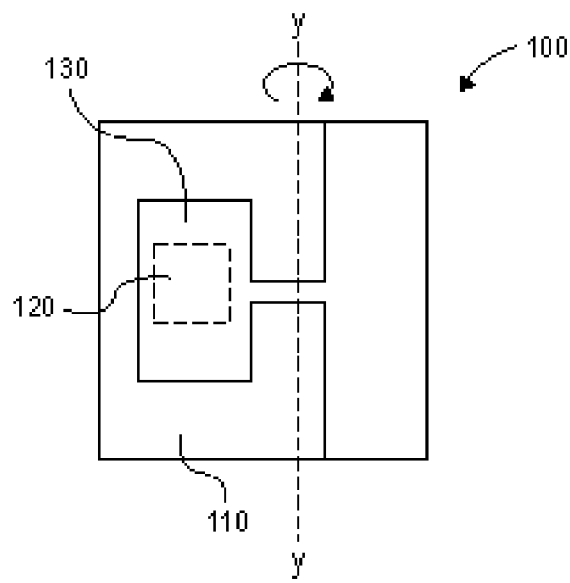

FIGS. 1A, 1B, and 1C show views of a hydrogel-actuated sensor module, according to an embodiment of the invention. FIG. 1A shows a side view of the module, while FIG. 1B shows a top view of the module, as indicated by the '1B' directional arrows in FIG. 1A. FIG. 1C also shows a top view, but of a slightly different version of the module. In the illustrated module 100, a base 110 may be used to support the remaining elements of the module. In some embodiments the base may be made of glass, but other embodiments may use other materials (e.g., silicon). A thin, deformable, and substantially planar member 130 may be attached to the base 110 where the two are in contact with each other, with a generally open space between the base and the member in the unattached areas. In some embodiments, the member 130 may be very thin, such as between 1-3 micrometers, but some embodiments of the invention are not limited to that range of thickness. A hydrogel substance 120 may also be attached to the base 110 as shown. As used herein, the term "hydrogel" may be defined as a porous crosslinked-polymer material that can absorb a substantial amount of liquid compared to its own dry volume. (As an example, soft contact lenses for vision correction are generally made of a hydrogel substance). The hydrogel substance 120 may be such that its thickness (as measured between the base 110 and the member 130) changes based on one or more particular characteristics of a liquid that permeates the hydrogel substance. Different types of hydrogel material may respond to different types of characteristics. For example, the thickness of the hydrogel may vary based on things such as, but not limited to: 1) the pH (a measurement of the acidity or alkalinity) of the liquid, 2) the temperature of the liquid, 3) the glucose concentration of the liquid, 4) the salt concentration of the liquid, 4) etc.

FIG. 1A shows the hydrogel substance 120 in physical contact with the member 130, but this may vary depending on the amount of liquid within the hydrogel substance, and the characteristics of that liquid. For example, in some embodiments the hydrogel substance 120 may be in contact with the member 130 when the hydrogel is permeated with a liquid having a characteristic that is within the desired range of measurement, but may or may not be in contact under other conditions. In some embodiments the hydrogel substance 120, when attached to the base, may be too thin to reach the member 130 when the hydrogel is dry (e.g., immediately after the module 100 is manufactured), but will be in contact with the member 130 when the hydrogel is permeated with a liquid. In other embodiments the hydrogel may be in contact with the member at all times, and may even be attached to the member. In these and many other embodiments, the hydrogel should be in contact with the member when the characteristic of the liquid is within the range that the module is designed to measure. An exception to this may be when the module is designed to produce a binary output, i.e., it will only detect whether the desired characteristic is above or below a particular threshold value. In such a case, it may not matter if the hydrogel is in contact with the member throughout the entire range of possible values, as long as the member deflects sufficiently to determine which side of the threshold value the liquid characteristic is on.

In the illustrated examples of FIGS. 1B and 1C, it can be seen that the member 130 may have three distinct functional areas. A non-movable area (the right-hand portion as shown in the figures) may be rigidly fastened to the underlying base. A moveable reflective area (the left-hand portion in the figures) may be the portion whose change in angle is detected by a change in the direction of a light beam reflected from the surface of the reflective area. A center flexible portion (the thin connecting arm between the non-movable area and the moveable reflective area) may be thin and/or narrow enough so that it will deflect when very little force is directed against the reflective area by the hydrogel substance. The reflective area and the center flexible portion together form a "T" shape in the example. In FIG. 1B the hydrogel is positioned beneath the reflective area in a position such that, when the thickness of the hydrogel expands and presses up against the member 130, the hydrogel will raise one arm of the T but not the other, so that the reflective area will twist slightly about the indicated axis "X-X". By contrast, in FIG. 1C the hydrogel is positions beneath the center of the reflective area such that, when the thickness of the hydrogel expands and presses against the member 130, the hydrogel will raise both arms of the "T" approximately the same amount, so that the reflective area will rotate slightly about the indicated axis "Y-Y". Other embodiments may shape and position the member 130 in other ways with respect to the hydrogel. In both of these examples, the member 130 has a thin flexible portion that is very narrow, so that a very small amount of pressure from the hydrogel may cause the member to deflect. Other configurations may also be used. Regardless of the specific configuration used, when the thickness of the hydrogel expands against the member 130, the plane of the reflective surface of member 130 should deflect to a different angle. When the plane of the top surface changes to a different angle, the direction of a light beam reflected from that surface should also change.

At least a portion of the top surface of the member 130 should have a smooth reflective characteristic, so that a narrow beam of light that is directed to the top surface will reflect in a predictable manner without undue scattering of the reflected light. Some embodiments may accomplish this by creating a highly-polished surface on the material of the member (e.g., polished silicon). Other embodiments may add a highly reflective layer to the top surface (e.g., aluminum). Still other embodiments may use other techniques to achieve the desired quality of reflectivity.

Figure 2:
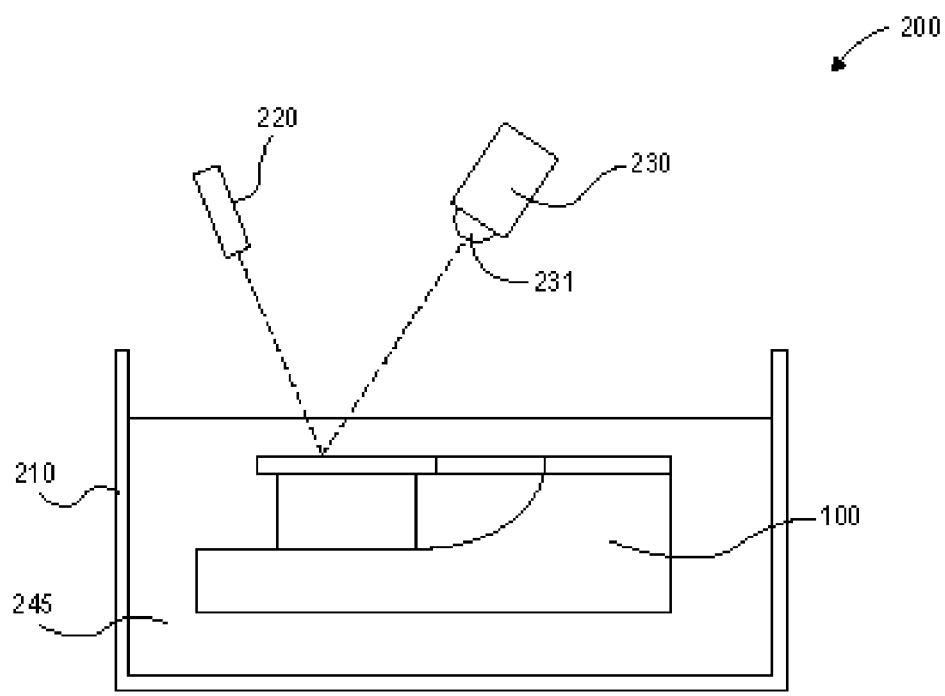
FIG. 2 shows a system containing a hydrogel-actuated sensor module, according to an embodiment of the invention.

FIG. 2 shows a system containing a hydrogel-actuated sensor module, according to an embodiment of the invention. In system 200, the hydrogel-based sensor module 100 from FIG. 1A is shown immersed in a liquid 245 that is contained in a container 210. A light source 220 is shown directing a narrow beam of light onto the top reflective surface of the module, and a light sensor module 230 is shown detecting the reflected light through at least one light sensor 231. In some embodiments, laser light may be used, although other embodiments may use other types of light. In some embodiments that only measure whether a characteristic of the liquid is within a narrow range, a single light sensor may suffice. For example, if the sensor detects light, the value is within range, but if it does not detect light, the value is out of range. But for measuring over a wider range of values, multiple sensors as described later for FIG. 3 may be used.

In the illustrated example, the container 210 is an open container, but other embodiments may use other techniques (e.g, the liquid 245 may be contained within a closed container). In the illustrated example, the light source 220 and light sensor 231 are external to the liquid, but other embodiments may use other techniques. For example, light source 220 and/or light sensor 231 may be located beneath the surface of the liquid 245, so that there is no air/liquid boundary to reflect, refract, scatter, or otherwise distort the light beam. In some embodiments, fiber optic extensions may be used to allow the electronics of the light source and light sensor to remain external to the liquid, while the output and inputs for the light beam are positioned within the liquid.

Although the illustrated embodiment of FIG. 2 shows a module that measures a characteristic of a liquid in a discrete container, other embodiments may configure the sensor module, light source, and light sensor in a package suitable for measuring the characteristic of a liquid in an open body of water (e.g., a lake or an ocean). Still other embodiments may be configured to measure a characteristic of a gaseous element rather than a liquid (e.g., measuring relative humidity of the air).

Figure 3:
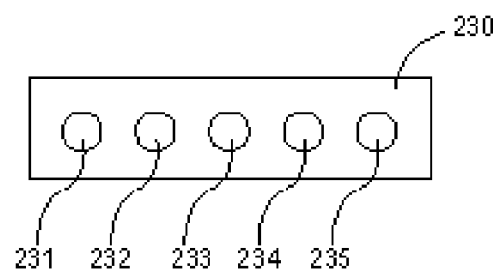
FIG. 3 shows a light sensor module with multiple light sensors, according to an embodiment of the invention.

FIG. 3 shows a light sensor module with multiple light sensors, according to an embodiment of the invention. The light sensor module in FIG. 3 is shown from the direction of the incoming light, rather than showing a side view as is done in FIG. 2. The illustrated light sensor module 230 is shown with multiple individual light sensors 231, 232, 233, 234, and 235, each of which may detect the reflected light beam if the reflected light beam impinges on that particular light sensor. This light sensor module may be positioned so that when the angle of the reflective surface of member 130 changes, and the light beam is thereby reflected in a slightly different direction, a different one of the multiple light sensors will detect the reflected beam. The light sensor that is detecting the light beam (or the light sensor that detects the strongest reading if multiple light sensors are simultaneously detecting the light beam), may be used to determine the angle of the planar reflective surface of the member 130. This may indicate the thickness of the hydrogel substance 120, which in turn may indicate a particular characteristic of the liquid 245 being tested.

The light sensor module of FIG. 3 uses a linear row of separate light sensors, but other embodiments may use other techniques. For example, some embodiments may use a matrix of separate light sensors. Other embodiments may use a single light sensor with a large sensor area that has different sensitivity across it's surface, so that the strength of the signal from the sensor will indicate which portion of that surface is receiving the beam. In still other embodiments, an expanding light beam may be used, configured so that the concentration of light decreases as you move further from the center of the beam. Thus, the relative intensity of the detected light would indicate the distance from the center of the light beam, and therefore indicate how much the center of the light beam has deviated from its reference position. Any type of feasible light sensing may be used, provided it indicates, directly or indirectly, how much the angle of the reflected light beam deviates from a known reference angle.

The amount that the thickness of the hydrogel changes over the desired range of measurement may depend on various factors, such as but not limited to: 1) the specific hydrogel substance used, 2) the overall basic thickness of the hydrogel substance (e.g., a 6-micrometer thick hydrogel might increase its thickness approximately twice as much as a 3-micrometer thick hydrogel when both are in the same liquid), 3) the type of characteristic being measured, 4) etc. In some embodiments the thickness may vary by only a few micrometers over the desired range of measurement (e.g., less than 5 micrometers, or less than 10 micrometers). In such instances, various techniques may be used to assure sufficient accuracy with these small dimensions. These techniques may include, but are not limited to: 1) using a very narrow-beam laser light, 2) making sure the reflective surface of the flexible member is smooth and planar within small tolerances, 3) immersing the light source and light sensor in the liquid to eliminate distortions at a liquid/air interface, 4) taking multiple measurements with multiple modules and applying statistical treatment to the multiple results (e.g., averaging, ignoring outlying values, etc.) to produce a representative value for the characteristic, 5) etc.

Once a result has been obtained from the aforementioned module and procedures, addition measures may be taken, depending on what that result indicates. For example: 1) if the pH of the water in a swimming pool is out of range, chemicals may be added to the water to correct the pH, 2) if the glucose level of a diabetic patient is out of range, the patient may take appropriate measures to correct his/her glucose level, 3) if the salt concentration of a saltwater solution is too high, the solution may be changed to reduce the salt concentration, 4) if the temperature of a liquid is too cool, heat may be added to the water to warm it up, 5) etc.

To achieve a quick-responding module, a hydrogel substance with very small dimensions may be used to reduce the time it takes for the liquid to permeate throughout the hydrogel (for example, single-digit micrometers for the thickness of the hydrogel and/or for the other dimensions of the hydrogel), with other dimensions of the module sized for compatibility with the hydrogel dimensions. To achieve these small dimensions, in some embodiments semiconductor processing techniques may be used to manufacture the sensor module.

Figure 4A:
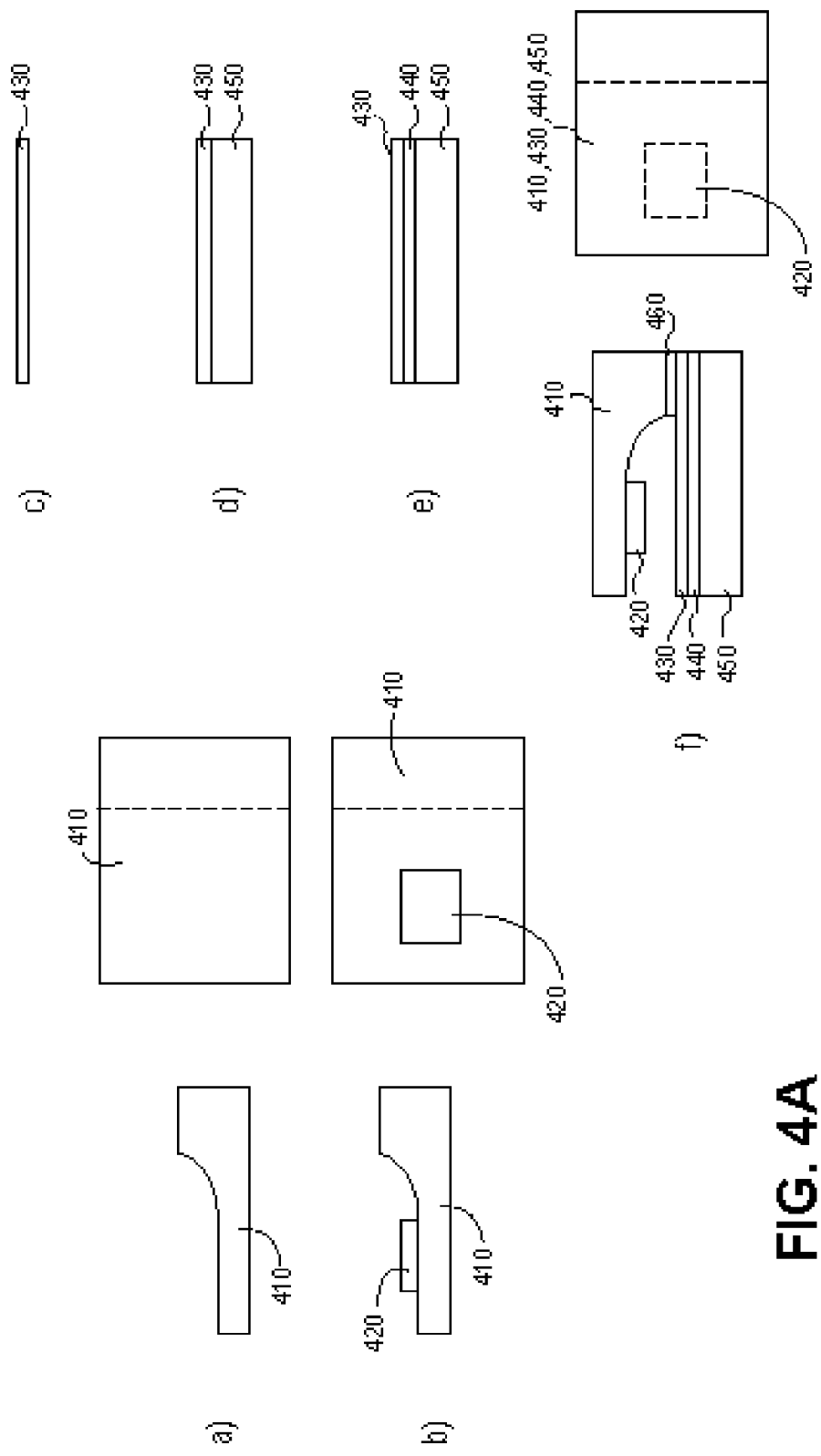
FIGS. 4A and 4B show a manufacturing process for a hydrogel-actuated sensor module, according to an embodiment of the invention.
Figure 4B:
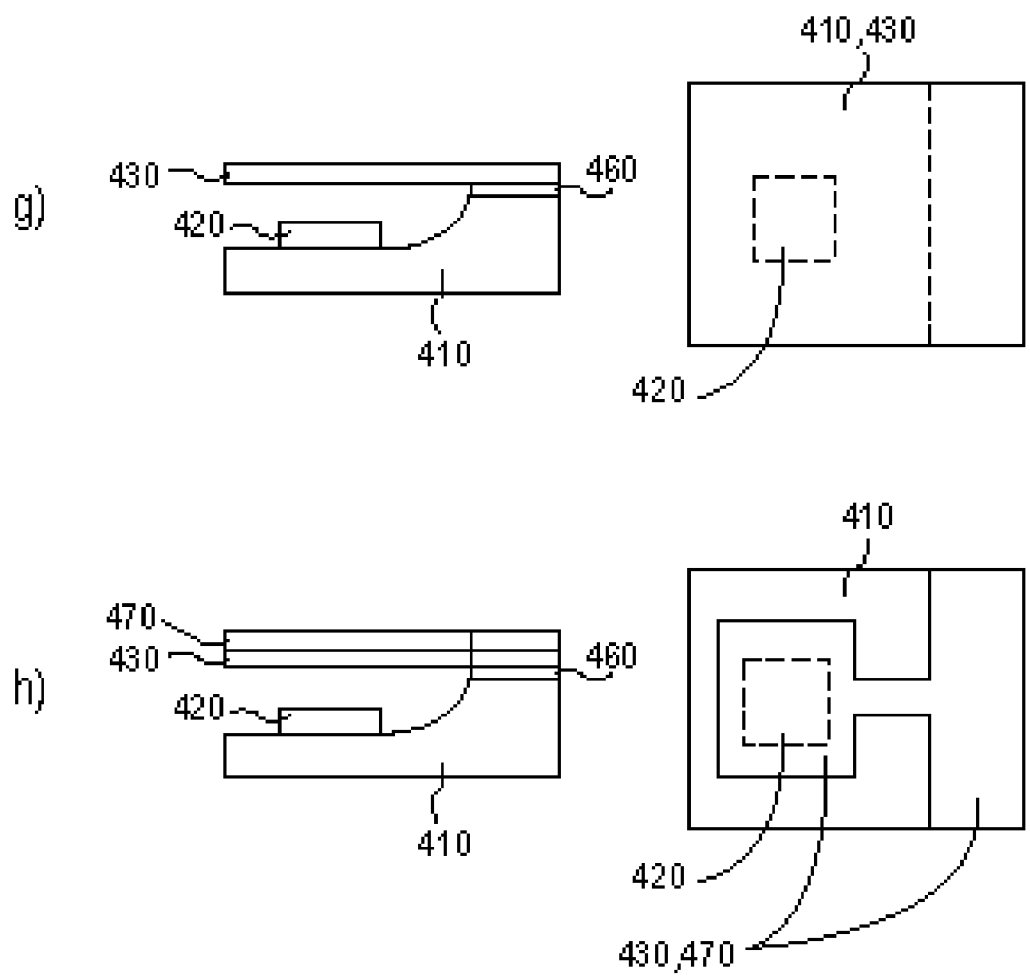

FIGS. 4A and 4B show a manufacturing process for a hydrogel-actuated sensor module, according to an embodiment of the invention. In the illustrated process, two sub-modules may be separately formed and then joined together for subsequent processing. Formation of the hydrogel sub-module, comprising a base and the hydrogel substance, is shown in steps a) and b), while various forms of the flexible member sub-module are shown in steps c) through e). Steps f) through h) show the joining of those two sub-modules into a single module, and the subsequent processing on that module. Steps a), b), f), g), and h) show both a side view and a top view to better illustrate the structure at each step. Steps c), d), and e) only show the side view, as there are no features in the structure that would be visible from the top view. The illustrated steps of FIGS. 4A, 4B show the fabrication of a single module, but in some processes multiple modules may be formed concurrently on a single base and/or single substrate by repetitive patterning of the single module, and the finished modules may later be separated by cutting the larger structure into the individual modules.

Step a) shows the formation of a two-level base 410, with the upper level for subsequent attachment to the flexible member and the lower level for subsequent attachment to the hydrogel. The two levels may be created in various ways. For example, a single piece of uniform thickness may be patterned and selectively etched to produce the lower level. Alternatively, a smaller upper piece may be attached to a larger lower piece to produce the two levels. The base may be composed of various materials, such as but not limited to glass or a silicon compound. Regardless of how the base 410 is formed, a hydrogel substance 420 may be attached or formed at step b). In some embodiments, the hydrogel may be formed in place through a process of deposition, lithographic patterning, exposure, and removal.

Separately, the flexible member sub-module may be produced in various forms. Three different examples are shown at steps c), d), and e), but other embodiments are also possible. Step c) shows a thin silicon wafer 430. Step d) shows a nitride or oxide layer 430 on a silicon substrate 450. Step e) shows a Silicon-On-Insulation (SOI), with a silicon layer 430 over an oxide layer 440 on top of an insulator 450.

The hydrogel sub-module and the flexible member sub-module may be attached to each other in step f) by attaching base 410 to layer 430. The flexible member sub-module of step e) is shown as an example, but any version of the flexible member sub-module may be used. Attachment may be accomplished in various ways, such as but not limited to: 1) an adhesive layer 460, 2) heat or chemical fusion of base 410 and layer 430, 3) etc. At step g), any layer or material above layer 430 may be removed by etching/thinning down the wafer. This removal of material may be accomplished through various techniques, such as but not limited to: 1) chemical etching, 2) plasma etching, 3) chemical mechanical polishing (CMP), 4) etc. If necessary, layer 430 may also be further thinned down by these and/or other processes. If the exposed surface of flexible layer 430 is not sufficiently reflective, it may be further treated to form a reflective surface through any suitable technique, such as but not limited to: 1) polishing the exposed surface, 2) depositing a reflective layer 470 (e.g., aluminum) on the flexible layer 440, 3) etc.

At step h), combined layers 430, 470 (or layer 430 alone if there is no layer 470), may be patterned into the necessary shape, such as the "T" shape shown in the top view of step h). This patterning may be accomplished through various means, such as but not limited to lithographic patterning and chemical or plasma etching. If multiple modules were formed on a single structure (e.g., similar to multiple integrated circuit dice being formed on a single wafer in a semiconductor fabrication process), the structure may be cut into individual modules subsequent to step h).

The foregoing description is intended to be illustrative and not limiting. Variations will occur to those of skill in the art. Those variations are intended to be included in the various embodiments of the invention, which are limited only by the spirit and scope of the following claims.

What is claimed is:

1. An apparatus, comprising:
    a substantially planar member attached to a base at a first portion and with a second portion whose distance from the base is controlled by a thickness of a hydrogel substance, such that the thickness of the hydrogel substance affects an angle of the plane of the second portion of the member;
    wherein the second portion has a reflective surface;
    wherein the angle of the plane affects an angle of light reflected from the reflective surface.

2. The apparatus of claim 1, further comprising the hydrogel substance having a range of thickness, a particular thickness within the range of thickness being dependent on a characteristic of a liquid contained within the hydrogel substance, the hydrogel substance positioned such that at least part of the range of thickness of the hydrogel substance places the hydrogel substance in contact with the member.

3. The apparatus of claim 2, wherein the characteristic of the liquid is selected from a list consisting of:
a pH;
a temperature;
a glucose concentration; and
a salt concentration.

4. The apparatus of claim 2, where a change in the thickness that is to correspond to a desired range of the characteristic of the liquid is less than 10 micrometers.

5. The apparatus of claim 1, further comprising:
a light source to direct the light onto the reflective surface; and
at least one light sensor to detect a change in the angle of the light reflected from the reflective surface.

6. The apparatus of claim 1, further comprising:
a container to contain the liquid such that the hydrogel substance is to be immersed in the liquid.

7. The apparatus of claim 6, further comprising the liquid in the container, such that the hydrogel substance is immersed in the liquid.

8. A method, comprising:
placing a module into a liquid, the module comprising
a hydrogel substance positioned to absorb a portion of the liquid; and
a flexible member with a reflective surface, the flexible member disposed such that a change in thickness of the hydrogel substance causes a change in a plane of the reflective surface;
wherein the thickness of the hydrogel substance indicates a value of a particular characteristic of the liquid;
reflecting a beam of light off the reflective surface;
detecting an angle of reflection of the reflected beam of light; and
measuring the angle of reflection to determine the value of the particular characteristic of the liquid.

9. The method of claim 8, wherein the particular characteristic is selected from a list consisting of:
a pH value;
a glucose concentration;
a temperature; and
a salt concentration.

10. The method of claim 8, wherein said reflecting a beam of light comprises reflecting a beam of laser light.

11. The method of claim 8, further comprising:
repeating the operations of placing, reflecting, detecting, and measuring, with multiple other modules; and
performing a statistical treatment on the results from the multiple modules to produce a result indicating a representative value for the characteristic.

* * * * *